United States Patent [19]

Smith et al.

[11] 4,038,429

[45] July 26, 1977

[54] ENHANCING CHEESE FLAVOR IN FOODS WITH A DIKETO-PIPERAZINE

[75] Inventors: Alistair Y. Smith, Geneva; Paul Dietrich, Chene-Bourg; Wilhelm Pickenhagen, Onex, all of Switzerland

[73] Assignee: Firmenich S.A., Geneva, Switzerland

[21] Appl. No.: 700,168

[22] Filed: June 28, 1976

[30] Foreign Application Priority Data

July 2, 1975  Switzerland .......................... 8589/75
Oct. 10, 1975  Switzerland ........................ 13499/75

[51] Int. Cl.$^2$ ............................................. A23L 1/226
[52] U.S. Cl. ............................. 426/537; 260/268 DK; 260/268 SY
[58] Field of Search ......................................... 426/537

[56] References Cited

U.S. PATENT DOCUMENTS

| 3,773,525 | 11/1973 | Pittet et al. ............................. 426/537 |
| 3,924,014 | 12/1975 | Ney et al. .......................... 426/537 X |
| 3,978,242 | 8/1976 | Freytag ................................. 426/537 |

*Primary Examiner*—Joseph M. Golian
*Attorney, Agent, or Firm*—Pennie & Edmonds

[57] ABSTRACT

A cheese flavor is improved or enhanced by the addition to food-products of a diketo-piperazine, defined as cyclo-(asparagyl-phenylalanyl); the typical "mouthfeel" character is thus developed.

A new process for the preparation of the said ingredient is also disclosed.

3 Claims, No Drawings

ENHANCING CHEESE FLAVOR IN FOODS WITH A DIKETO-PIPERAZINE

BACKGROUND OF THE INVENTION

The flavour industry has expended a great deal of efforts in an attempt to solve the problem of conferring to foodstuffs the characteristic taste of cheese products and the use of certain flavouring ingredients and compositions to reconstitute the full aroma of cheese has been disclosed. It is known for instance that certain lower fatty acids, lactones and phenols play a determinant role in such a reconstitution.

A number of flavouring compositions destined to develop the cheese flavour in different food products are at present commercialized. Up to now it has not been possible however to reproduce in a fully satisfactory way the whole character of the desired natural aroma.

One of the major obstacles which the flavourist has to overcome is in fact represented by the reconstitution of the genuine taste conferred by the so called "mouth-feel". This is a gustative character promoted by the ingestion of certain foods which convey the particular feeling felt at that moment by the consumer in his mouth and which is determined by the contact of the food on the mucous membrane of the tongue and the palate. Said gustative character is determinant of the taste of cheese and cheese products.

THE INVENTION

It has now surprisingly been found that this special character is essentially obtained by the addition to foodstuffs of a flavouring composition comprising effective amounts of a diketo-piperazine of formula

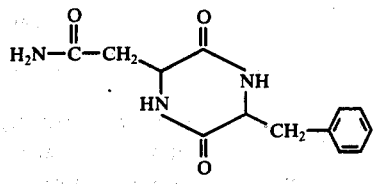
(I)

The present invention therefore relates to a flavouring composition destined to improve or modify the taste of foodstuffs by conferring thereto a cheese flavour, which comprises effective amounts of a diketo-piperazine of formula (I).

This invention relates further to a cheese, a cheese imitating or a cheese containing product comprising a taste effective amount of a diketo-piperazine of formula (I).

This invention provides further a process for improving or enhancing the gustative character of cheese type flavours in foodstuffs, which comprises adding thereto a small but effective amount of a diketo-piperazine of formula (I).

Our present discovery is particularly surprising. Recent investigations in fact have shown that certain diketopiperazine, namely a piperazine derivative of formula

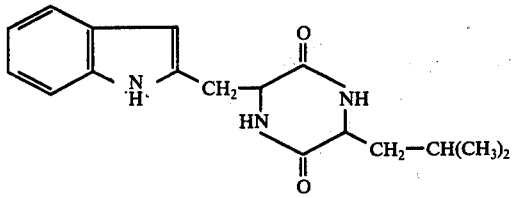

develop a bitter flavour character [see, J. Biochem. 72, 841 (1972) and Tetrahedron Letters 509 (1974)], and it is generally recognized that bitterness, usually induced in the products derived from milk fermentation by the action of certain bacteria, has to be avoided in cheese flavours [see for instance, Z. Lebensm. Unters, Forsch. 137, 370 (1968)].

Finally, the invention provides a process for preparing the diketo-piperazine of formula (I), which process comprises cyclizing aspartame by means of an acidic cyclizing agent, in a suspension or solution in a lower aliphatic alcohol, and subsequently treating the resulting reaction mixture with ammonia.

PREFERRED EMBODIMENTS OF THE INVENTION

According to a preferred embodiment of the process of the present invention suitable cyclizing agents include mineral and organic protonic acids, or cationic acidic resins. We have observed however that the best yields of the end product were achieved by carrying out the cyclization of aspartame in the presence of an acidic diatomaceous earth.

Suitable lower aliphatic alcohols include methanol, ethanol or propanol e.g.; methanol is preferred.

The cyclization is effected at a temperature higher than the boiling temperature of the chosen alcohol, and consequently it is necessary to operate at a pressure higher than the atmospheric pressure. Preferred temperatures are of from about 100° to about 150° C, while the reaction is carried out in an autoclave. According to a preferred embodiment of the invention, the reaction mixture, resulting from the cyclization of aspartame is treated, after cooling, with an excess of ammonia, whereupon the whole is kept at about 80°–120° C for a time interval sufficient to promote the aminolysis reaction.

By the process of the invention the end product is obtained with high yields with relatively simple technical procedure.

Moreover, the said process offers a clear advantage over analogous known preparation procedures — see, e.g., German Offenlegungsschrift 2,445,674 — inasmuch as the two reaction steps, which characterize it, can be carried out in a subsequential manner in the same reactor. In such a way the number of manipulations required are sensibly reduced and, consequently, the production costs are lowered.

The said process may be illustrated by the following reaction scheme:

(III)

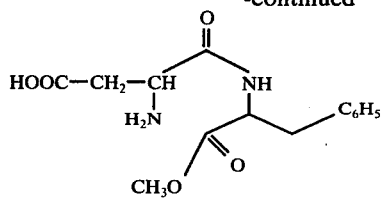

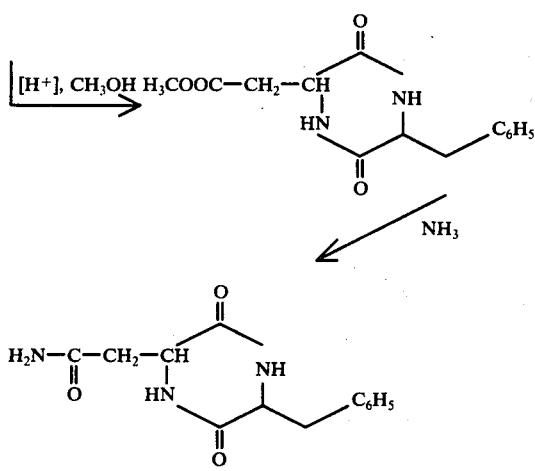

Aspartame, also defined as the methyl ester of aspartyl-phenylalanine, is a commercial product which, e.g. can be synthesized in accordance with the process described in British Patent No. 1,152,977.

The diketo-piperazine of the invention is chemically defined as cyclo-(Asn-Phe) or cyclo-(asparagyl-phenylalanyl-) It is a known compound and its synthesis was described for the first time in Hoppe — Seyler's Z. physiol. Chem. 174, 76 (1928). Due to the presence of asymmetric carbon atoms in its molecule, compound (I) can occur in the form of one of the configurational isomers more precisely defined according to:
cyclo-(D-Asn-L-Phe),
cyclo-(D-Asn-D-Phe),
cyclo-(L-Asn-D-Phe) and
cyclo-(L-Asn-L-Phe)

or according to any mixture thereof.

For all practical purposes, in view of the similarity of their organoleptic properties, at least insofar as their use in the field of the invention is concerned, any of the above said isomers or any mixture thereof can be used satisfactorily.

The proportions according to which compound (I) can be used in accordance with the invention vary within a wide range. Preferably, quantities of about 10 to 200 ppm (parts per million), based on the total weight of the flavoured material, are used. However, proportions beyond these limits can be employed depending upon the specific nature of the material to be aromatized and the flavouring effect it is desired to achieve.

When compound (I) is used for the manufacture of artificial flavour compositions in admixture with other flavour ingredients, proportions of 5 up to about 50% by weight of the composition can be suitably used.

On manufacturing cheese flavour compositions, suitable coingredients include, e.g., lactic, butyric and isovalerianic acid, as well as methyl-pentyl-ketone and the lactone derivatives of lower hydroxy-carboxylic acids. The resulting flavour compositions can be suitably added to the foodstuff in the form of a solution, a dispersion or an emulsion in water, alcohol or in an edible oleaginous liquid vehicle.

The invention is better illustrated by, but not limited to, the following examples wherein the temperatures are indicated in degrees centigrade.

EXAMPLE 1

50 g of aspartame in 1000 ml of methanol in the presence of 0.5 g of acidic diatomaceous earth were heated at 135° in an autoclave for about 60 hours. In such a way, 98% of the starting material was converted into a diastereoisomeric mixture of the compound of formula (II) — see above given reaction scheme. The resulting reaction mixture was then cooled to about 30° and at that temperature 100 g of gaseous ammonia were added, and the whole was kept at 100° for 7 hours, whereupon, it was filtered and concentrated. The obtained residue (42.9 g) (yield 98%) constituted by a brownish solid, comprised about 85% of the desired product.

A crystallization in 250 ml of water gave 27 g (yield 61%) of a diastereoisomeric mixture of cyclo-(asparagyl-phenylalanyl-).

EXAMPLE 2

Two flavouring compositions for imparting a cheese type flavour were obtained by mixing together the following ingredients (parts by weight):

|  | Control | |
| --- | --- | --- |
|  | A | B |
| Butyl-butyryl lactate | 0.20 | 0.20 |
| Isovalerianic acid | 0.50 | 0.20 |
| Ethyl butyrate | 0.20 | 0.20 |
| Butyric acid | 1.20 | 0.20 |
| Lactic acid | 0.10 | — |
| Caproic acid | 0.60 | 0.10 |
| Propylene glycol | 7.20 | 9.00 |
| Methyl-pentyl ketone | — | 0.10 |
|  | 10.00 | 10.00 |

The above compositions (0.1g) were separately used for aromatizing 1000 ml of salty water made up by dissolving 5 g of sodium chloride in 1 l water, which aromatized product was then evaluated by a panel of experts.

Two samples of 0.1 g each of the said compositions were separately mixed with 0.1 g of cyclo(Asn-Phe) to give two novel flavour compositions A' and B' defined as "test" compositions. Their organoleptic properties were determined by carrying out an evaluation test in much the same way as indicated for the control compositions.

The evaluation panel unanimously declared that the materials aromatized with the "test" compositions possessed, in contradistinction with those flavoured by means of the "control" compositions, a very satisfactory "mouth-feel" character.

What is claimed is:

1. A cheese, a cheese-imitating or a cheese-containing product having added thereto from about 10 to 200 ppm of a diketo-piperazine of the formula

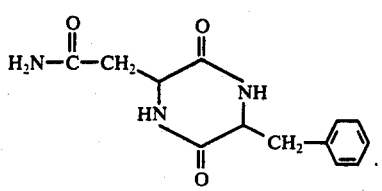
(I)

2. A process for imparting a mouth feel character of cheese type flavours to foodstuffs which comprises adding thereto from about 10 to 200 ppm of a diketo-piperazine of the formula

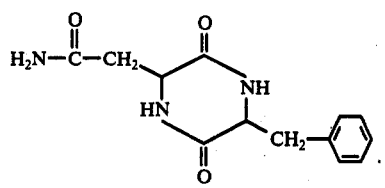
(I)

3. A process for improving or enhancing the gustative character of cheese type flavours in foodstuffs which comprises adding thereto from about 10 to 200 ppm of a diketo-piperazine of the formula

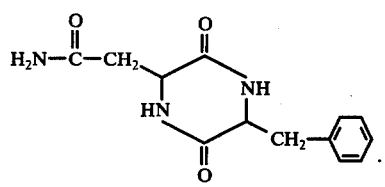
(I)

* * * * *